United States Patent [19]
Hilscher

[11] 3,956,348
[45] May 11, 1976

[54] STEROID ETHER SPLITTING
[75] Inventor: Jean-Claude Hilscher, Berlin, Germany
[73] Assignee: Schering Aktiengesellschaft, Berlin & Bergkamen, Germany
[22] Filed: Feb. 25, 1975
[21] Appl. No.: 552,960

[30] Foreign Application Priority Data
Feb. 27, 1974  Germany............................ 2409991

[52] U.S. Cl............................ 260/397.5; 260/397.4; 260/239.55 C
[51] Int. Cl.².......................................... C07J 1/00
[58] Field of Search...................... 260/397.4, 397.5

[56] References Cited
UNITED STATES PATENTS

| | | | |
|---|---|---|---|
| 3,818,056 | 6/1974 | Pierdet et al. ................. | 260/397.45 |
| 3,845,084 | 10/1974 | Stein............................... | 260/397.5 |

*Primary Examiner*—Elbert L. Roberts
*Attorney, Agent, or Firm*—Millen, Raptes & White

[57] ABSTRACT

Ethers of aromatic steroids are cleaved to regenerate the hydroxy group with aluminum hydride, dialkylaluminum hydride or trialkylaluminum.

10 Claims, No Drawings

STEROID ETHER SPLITTING

BACKGROUND OF THE INVENTION

This invention relates to a process for cleaving aromatic steroid ethers.

The splitting of ethers of aromatic alcohls requires, as is known, more vigorous conditions and reagents than the splitting of purely aliphatic ethers. Frequently, alkyl ethers are utilized in steroid syntheses for the protection of hydroxy groups, because this grouping withstands almost all reactions. However, precisely because of this great resistance displayed by these ethers against reagents, difficulties are often encountered in the liberation of the hydroxy groups protected by such etherification after the synthesis, without affecting other groups of the molecule during this step. The aromatic steroid ethers are particularly resistant. They are split only under extreme reaction conditions, such as, for example, by treatment with strong acids, such as hydrogen bromide in glacial acetic acid (See German Unexamined Laid-Open Application DOS 1,924,222) or with a hydrochloric acid-pyridine complex at high temperatures. See J. Chem. Soc. (London), 1963, 5072; Ann. Chem. 705 (1967) 211. However, many steroid ethers are sensitive to acids, for example, those wherein acids can cause rearrangements or shifting of double bonds. The only known method for splitting of aromatic steroid ethers which is not conducted in an acidic medium employs Grignard reagents at temperatures of about 160° C. See Tetrahedron 26 (1970) 1917.

Accordingly, it is an object of this invention to provide a process for splitting of ethers of aromatic steroid alcohols, particularly those with at least one additional double bond in the steroid molecule which can be conducted under non-acidic, gentle conditions, and thus which does not have the aforedescribed disadvantages. Other objects will be apparent to those skilled in the art.

SUMMARY OF THE INVENTION

According to this invention, ethers of aromatic steroid alcohols, including those which contain at least one further double bond in the steroid molecule and which are thus especially sensitive to acids and which do not withstand excessively high temperatures, are cleaved to regenerate the aromatic hydroxy group by reaction with an alkyl aluminum compound or aluminum hydride of the formula $AlR_1R_2R_3$ wherein $R_1$, $R_2$ and $R_3$ are alike or different and are hydrogen or straight-chain or branched-chain alkyl.

It was surprising that further double bonds in the steroid molecule, i.e., those which are not part of the aromatic ring system, are not concomitantly reduced. A reduction of non-aromatic double bonds would have to be expected, in accordance with the published work of Ziegler et al. (liebigs Ann. Chemie, 589, 105, 159), since alkyl aluminum compounds, such as diethylaluminum hydride, attack cyclic olefins.

DETAILED DISCUSSION

Preferred aluminum compounds of the formula $AlR_1R_2R_3$ are those wherein $R_1$ and $R_2$ are alike and are alkyl of 1–4 carbon atoms and $R_3$ is H or $R_1$, especially those wherein $R_1$ and $R_2$ are ethyl, n-butyl or isobutyl, particularly those wherein $R_1$ and $R_2$ are isobutyl.

Preferred starting steroids are those wherein the A-ring is aromatic, particularly those wherein the ether group is in the 1, 2 or 3-position thereof, especially the 3-position.

Specific examples of alkyl aluminum compounds of the formula $AlR_1R_2R_3$ are triisobutylaluminum, diethylaluminum hydride, di-n-butylaluminum hydride, and diisobutylaluminum hydride. Aluminum hydride is also suitable.

The reaction is conducted in an inert solvent in which the starting steroid is at least partially soluble. Solvents which can be used for the process of this invention are those which are inert with respect to the reactants and which have a boiling point below 160° C. Examples are aromatic hydrocarbons, such as benzene, toluene, and xylene; aliphatic hydrocarbons, such as hexane; cyclic hydrocarbons such as cyclopentane and cyclohexane; and their mixtures, as well as, for example, ligroin and benzine.

The exact nature of ether group to be cleaved is not critical. The ether group is preferably an alkyl ether of an alkanol of 1–4 carbons, preferably a methyl or ethyl ether. However, all other ethers conventional in steroid chemistry can be employed, including those more readily cleaved than alkyl ethers, e.g., benzyl ethers. Specific examples of ether groups are methoxy, ethoxy, isopropoxy, n-butoxy, benzyloxy and cyclopentyloxy.

The ether group or groups can be at any possible position of the steroid molecule, such as, for example in the 1-, 2-, 3-, 6-, 7-, 11-, 16- and 17-positions.

The steroid ethers employed as the starting material have an ether substituent on an aromatic ring, preferably an aromatic A-ring. Preferred are those having at least one further double bond in the steroid molecule which can be conjugated or non-conjugated with respect to the aromatic A-ring, such as, for example, in the 6-, 7-, 8-, 9(11)-, 14-and/or 16-position. Moreover, the rings of the steroid molecule can be substituted in the usual manner, such as, for example, with lower alkyl groups, preferably methyl, e.g., in the 1-, 2-, 4-, 6-, 7-, 13-, 16- and 17-positions and free or esterified hydroxy groups in the 1-, 2-, 3-, 4-, 6-, 7-, 8-, 11-, 16-, 17-, 20- and/or 21-position.

The starting steroid ethers can be ethers of steroids of, e.g., the estrane, the 18-lower-alkyl-estrane, and the 19-norpregnane series.

Preferred as starting steroids are A-ring aromatic steroids, e.g., of the formula

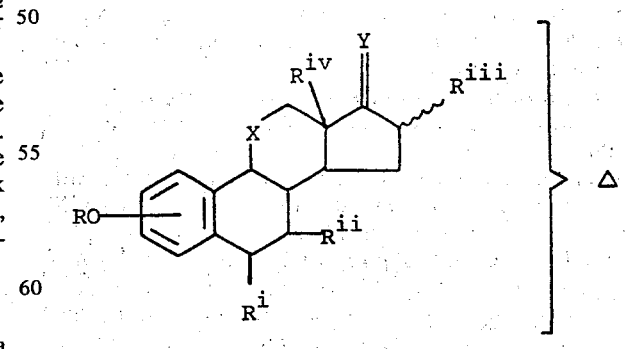

wherein R is lower-alkyl, preferably methyl, or benzyl; $R^i$ and $R^{ii}$ each are hydrogen or lower-alkyl, preferably methyl; $R^{iii}$ is hydrogen or α- or β-methyl; $R^{iv}$ is hydrogen or lower-alkyl, preferably methyl or ethyl; X is C=O or $CH_2OH$ and Y is C=O, $CR^{ii}$,

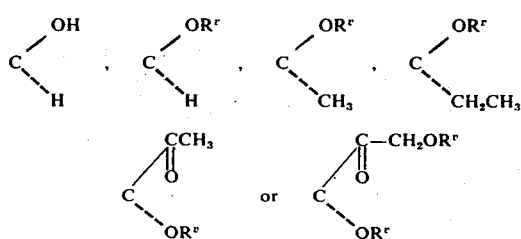

wherein $R^v$ is hydrogen, the acyl radical of an organic carboxylic acid, preferably containing one to 20, most preferably one to eight carbon atoms, and Δ is a double bond optionally present in one or more of the 6-, 7-, 8-, 8(14)-, 9(11)-, 14-, 15- or 16-positions.

By the process of this invention, it is possible to split aromatic steroid ethers which do not withstand high temperatures and are sensitive to acids, since the process of this invention is gentler and also simpler in its conductance as compared to the conventional steroid ether splitting process using Grignard reagents.

While carbon-to-carbon double bonds present in the steroid molecule are not attacked, carbonyl oxygen atoms are reduced to hydroxy groups. As will be apparent, any such reducible groups in the starting steroid, e.g., ester, ketone, ketalized ketone, aldehyde, epoxide, etc., are susceptible to being and probably will be reduced concurrently with the cleavage of the ether group. Accordingly, if any such groups are present in the molecule, a correspondingly larger amount of aluminum compound may be required to both reduce such reducible group and cleave the ether group.

Surprisingly, if an attempt is made to block a keto group to prevent its reduction, for example, by ketalization, such as an ethylenedioxy group, an ether bond thereof is split, and a 2-hydroxyethoxy steroid is first obtained, which is cleaved into the corresponding hydroxy compound if the reaction is continued extensively.

Ester groupings, such as the formyloxy group, for example, are reductively saponified under the conditions of the process according to the present invention.

If a free hydroxy group is present in the molecule of the steroid ether, especially a phenolic hydroxy group, a corresponding excess of the aluminum compound is also required, since part of this reactant is bound by complex formation. These complexes, however, are hydrolyzed during the course of the working-up step to which the reaction mixture is subjected, to regenerate the hydroxy group.

The process of this invention is advantageously carried out by dissolving and/or suspending the steroid ether in the inert solvent, gradually adding the alkyl aluminum compound or the aluminum hydride, with the exclusion of air, and slightly heating the reaction mixture. The reaction temperature can optionally be raised to the boiling point of the solvent or solvent mixture. Although the splitting reaction starts already at room temperature, it is advantageous to heat the reaction mixture in order to increase the reaction rate of the ether splitting step, e.g., 40° to 70° C. The aluminum compound is suitably added in a molar equivalent excess. Normally 1.1 – 3 moles of aluminum compound are used per mole of steroid ether grouping, plus additional amounts as required due to the presence of other groups in the steroid molecule reactive with the aluminum compound. After the reaction is terminated, the excess aluminum compound is decomposed, for example, with alcohol, and then with aqueous alcohol. Thereafter, the steroid product is isolated from the reaction mixture, e.g., by distillation of the solvents and precipitation into water, drying the precipitate and extraction with an organic solvent. In case of steroid alcohols stable with respect to dilute acids at lower temperatures, the reaction mixture, after the excess aluminum compound has been decomposed, can immediately be precipitated into dilute acid, e.g., 2% strength hydrochloric acid, and then washed neutral with water after filtration. The further working-up operation and purification take place according to conventional methods, such as, for example, recrystallization and chromatography.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

10.0 g. of 3-methoxy-1,3,5(10),7-estratetraen-17β-ol is suspended in 100 ml. of dry toluene. Within 20 minutes, 125 ml. of a 20% diisobutylaluminum hydride solution in toluene is added dropwise thereto under nitrogen purging and agitation at 20° C. Under further nitrogen purging and agitation, the reaction mixture is heated for 6 hours under reflux. Then, the mixture is cooled to about 0°C. Under ice cooling and while continuing the nitrogen purging, 25 ml. of ethanol and then 25 ml. of an ethanol-water mixture (1:1) is added dropwise to decompose the aluminum compound. The mixture is agitated for another 30 minutes at 20° C. Then, the solvents are distilled off under vacuum. The residue is made into a slurry with 100 ml. of methanol and precipitated into 500 ml. of water. The solids are filtered off, washed with water, and dried. The dry residue is extracted with chloroform. One gram of active carbon is added to the chloroform solution and, after the carbon has been filtered off, the solution is concentrated to 30 ml. During cooling, 8.84 g. of 1,3,5(10),7-estratetraene-3,17-diol is crystallized; m.p. 173°–175°0 C.; $[\alpha]_D = +208.6°$ (dioxane); $\epsilon_{280} = 2160$.

EXAMPLE 2

1.0 g. of 3-methoxy-1,3,5(10),7-estratetraen-17β-ol is suspended in 10 ml. of xylene. Under agitation and nitrogen purging 18.5 ml. of triisobutylaluminum (20% in xylene) is added within 5 minutes, and the reaction mixture is heated for 28 hours under reflux. After cooling, the decomposition step is carried out at about 0° C. with 5 ml. of ethanol and then with 5 ml. of an ethanol-water mixture (1:1). The further working-up and purification steps take place as described in Example 1. Yield: 0.68 g. of 1,3,5(10),7-estratetraene-3,17β-diol; m.p. 172°–175° C.; $[\alpha]_D = +208.1°$ (dioxane); $\epsilon_{279} = 2080$.

EXAMPLE 3

1.0 g. of 3-methoxy-1,3,5,(10),7-estratetraen-17β-ol is suspended in 10 ml. of toluene. At room temperature, under agitation and nitrogen purging, 12.5 ml. of a 20% diethylaluminum hydride solution in toluene is added within 10 minutes. The reaction mixture is then heated under reflux for 75 minutes with agitation and further nitrogen purging. Then, the mixture is cooled to about 0° C. and decomposed first with 3 ml. of ethanol and thereafter with 3 ml. of an ethanol-water mixture (1:1). The mixture is stirred for another 10 minutes at room temperature. The solvents are distilled off under vacuum, the residue is made into a slurry with 10 ml. of methanol and precipitated into 50 ml. of water. The mixture is then filtered, washed with water, and the residue is dried. The dry product is extracted with chloroform, concentrated under vacuum to 3 ml., and crystallized, thus obtaining 0.87 g. of 1,3,5(10),7-estratetraene3,17β -diol; m.p. 174°-176° C.; $[\alpha]_D = +210.8°$ (dioxane); $\epsilon_{280} = 2130$.

EXAMPLE 4

1.0 g. of 3-methoxy-1,3,5-(10),7-estratetraen-17β-ol is heated in 10 ml. of toluene with 12.5 ml. of di-n-butylaluminum hydride (20% in toluene) for 4 hours under reflux and nitrogen purging. The reaction mixture is decomposed and worked up as set forth in Example 3, thus obtaining 0.74 g. of 1,3,5(10),7-estratetraene-3,17β-diol; m.p. 174°-175° C.; $[\alpha]_D = +208.0°$ (dioxane); $\epsilon_{279} = 2160$.

EXAMPLE 5

0.9 g. of 3-methoxy-1,3,5(10),6,8-estrapentaen-17β-ol is heated under reflux in 9 ml. of toluene with 11 ml. of diisobutylaluminum hydride (20% in toluene) for 12 hours under nitrogen purging. The reaction mixture is decomposed and worked up as described in Example 3. The dried residue is extracted with a methylene chloride-methanol mixture. After the solvent has been evaporated, an oil remains which is crystallized with hexane, yielding 0.68 g. of 1,3,5(10),6,8-estrapentaene-3,17β-diol; m.p. 244°-246° C.; $[\alpha]_D = +55.8°$ (dioxane); $\epsilon_{257} = 3300$; $\epsilon_{267} = 4530$; $\epsilon_{280} = 5070$; $\epsilon_{289} = 3760$; $\epsilon_{324} = 2330$; $\epsilon_{337} = 2700$.

EXAMPLE 6

2.0 g. of rac.-3-methoxy-17β-methyl-14β-gona-1,3,5(10),6,8-pentaene is heated in 20 ml. of toluene with 25 ml. of diisobutylaluminum hydride (20% in toluene) for 5 hours under reflux and nitrogen purging. The reaction mixture is decomposed under ice cooling, first with 5 ml. of ethanol and then with 5 ml. of an ethanol-water mixtur (1:1). The mixture is stirred for another 10 minutes at room temperature, then the solvent is distilled off under vacuum and the residue made into a slurry with 20 ml. of methanol. This suspension is precipitated into 100 ml. of 2% hydrochloric acid, stirred for 15 minutes, filtered, and washed with water to render it neutral. Yield: 1.90 g. of rac.-3-hydroxy-17β-methyl-14β-gona-1,3,5(10),6,8-pentaene which, after purification, has a melting point of 125°-126° C.

$\epsilon_{227} = 63,200$; $\epsilon_{257} = 4060$; $\epsilon_{266} = 5060$; $\epsilon_{276} = 5370$; $\epsilon_{287} = 3730$; $\epsilon_{325} = 2000$; $\epsilon_{338} = 2410$.

EXAMPLE 7

2.0 g. of estradiol-3-methyl ether is heated under reflux in 20 ml. of toluene for 5 hours with nitrogen purging together with 25 ml. of diisobutylaluminum hydride (20% in toluene). The reaction mixture is decomposed and worked up according to Example 3 and purified from methanol-chloroform. Yield: 1.69 g. of estradiol; m.p. 172°-174° C.; $[\alpha]_D = +74.2°$ (dioxane); $\epsilon_{280} = 1990$.

EXAMPLE 8

2.0 g. of 3-methoxy-17β-formyloxy-1,3,5(10),7-estratetraene is refluxed in 20 ml. of toluene with 35 ml. of diisobutylaluminum hydride (20% in toluene) for 8 hours under nitrogen purging. The reaction mixture is decomposed under ice cooling first with 5 ml. of ethanol, then with 5 ml. of an ethanol-water mixture (1:1). The further working-up and purification steps are conducted as indicated in Exaple 3. Yield: 1.38 g. of 1,3,5(10),7-estratetraene-3,17β-diol; m.p. 173°-175° C.; $[\alpha]_D = +209.6°$ (dioxane); $\epsilon_{280} = 2100$.

EXAMPLE 9

2.0 g. of estrone-3-methyl ether is suspended in 20 ml. of toluene and heated under reflux and nitrogen purging for 4 hours with 30 ml. of diisobutylaluminum hydride (20% in toluene). The reaction mixture is decomposed and worked up as described in Example 6. After recrystallization from methanol-chloroform, 1.78 g. of estradiol is obtained; m.p. 174°-175° C.; $[\alpha]_D = +74.2°$ (dioxane); $\epsilon_{281} = 2080$.

EXAMPLE 10

0.70 g. of 2-methoxy-1,3,5 (10)-estratriene-3,17β-diol is heated under reflux and nitrogen purging in 10 ml. of toluene with 18 ml. of diisobutylaluminum hydride (20% in toluene) for 22 hours. The reaction mixture is cooled to about 0° C. and then decomposed with 5 ml. of ethanol and then with 5 ml. of ethanol-water mixture (1:1). The mixture is further worked up as set forth in Example 3. After purification from methanol, 0.45 g. of 1,3,5(10)-estratriene-2,3,17β-triol is obtained; m.p. 181°-183° C.; $\epsilon_{286} = 3420$.

EXAMPLE 11

2.0 g. of 3-methoxy-1,3,5(10),8-estratetraen-17β-ol is agitated in 20 ml. of toluene with 75 ml. of diisobutylaluminum hydride (20% in toluene) for 24 hours at 70° C. under nitrogen purging. The reaction mixture is decomposed and worked up as set forth in Example 3. The dried residue is extracted with methanol. After evaporation of the solvent under vacuum, an oil reamins which is crystallized with hexane. Yield: 1.44 g. of 1,3,5(10),8-estratetraene-3,17β-diol, m.p. 130°-135° C.; $[\alpha]_D = -11.4°$ (dioxane); $\epsilon_{276}$ 32 14,700.

The 1,3,5(10),8-estratetraene-3,17β-diacetate melts at 137°-140° C.; $[\alpha]_D = -45.7°$ (dioxane); $\epsilon_{277} = 14,400$.

EXAMPLE 12

1.0 g. of rac.-3-methoxy-18-methyl-1,3,5(10),8-estratetraen-17β-ol is stirred under nitrogen purging in 10 ml. of toluene with 12.5 ml. of diethylaluminum hydride (20% in toluene) for 72 hours at 40° C. The reaction mixture is decomposed and worked up as described in Example 3. The dried residue is extracted with a methylene chloride-methanol mixture (2:1). After the solvent has been evaporated under vacuum, an oil remains which is crystallized with hexane. Yield: 0.94 g. of rac.-18-methyl-1,3,5(10),8-estratetraene-3,17β-diol, m.p. 178°-181° C.; $\epsilon_{277} = 15,700$.

EXAMPLE 13

2.0 g. of 3-ethoxy-1,3,5(10),6,8-estrapentaen-17β-ol is heated under reflux and nitrogen purging in 4 ml. of toluene with 35 ml. of di-n-butylaluminum hydride (20% in toluene) for 24 hours. The reaction mixture is decomposed and worked up as indicated in Example 3. The dried residue is extracted with a methylene chloride-methanol mixture (2:1), concentrated to 6 ml., cooled, and the crystals vacuum-filtered, thus obtaining 1.73 g. of 1,3,5(10),6,8-estrapentaene-3,17β-diol, m.p. 242°–245° C. $[\alpha]_D = +52.0°$ (dioxane); $\epsilon_{258} = 3000$; $\epsilon_{268} = 4500$; $\epsilon_{279} = 4860$; $\epsilon_{290} = 3570$; $\epsilon_{326} = 2290$; $\epsilon_{339} = 2530$.

EXAMPLE 14

2.0 g. of 3-methoxy-1,3,5(10)-estratriene-8α,17β-diol is introduced, in 35 ml. of 17% diisobutylaluminum hydride solution, into toluene and heated for 4 hours under reflux, nitrogen purging, and agitation. The reaction mixture is decomposed and worked up as described in Example 3. The dried residue is extracted with a methylene chloride-methanol mixture (2:1), concentrated to dryness under vacuum, and crystallized from methanol. Yield: 1.45 g. of 1,3,5(10)-estratriene-3,8α,17β-triol, m.p. 228°–233° C. $[\alpha]_D = +30.6°$ (dioxane); $\epsilon_{279} = 1700$.

EXAMPLE 15

0.8 g. of 3-methoxy-20,20-ethylenedioxy-1,3,5(10)-pregnatrien-17-ol is heated under reflux and nitrogen purging in 10 ml. of toluene with 10 ml. diisobutylaluminum hydride (17% in toluene) for 3 ½ hours. The reaction mixture is decomposed and worked up as described in Example 3. The dried residue is extracted with a methylene chloride-methanol mixture (2:1), concentrated to dryness under vacuum, and crystallized with hexane, thus obtaining 0.54 g. of 20-(2-hydroxyethoxy)-1,3,5(10)-pregnatriene-3,17-diol, m.p. 163°–168° C. $[\alpha]_D = +24.8°$ (chloroform); $\epsilon_{281} = 1950$.

If the above reaction is not interrupted after 3 ½ hours of heating under reflux, but rather is continued for a reaction time of 20 hours, the yield is 0.51 g. of 1,3,5(10)-pregnatriene-3,17,20-triol. The substance is obtained as an oil. $\epsilon_{280} = 1940$.

EXAMPLe 16

2.0 g. of 1-methoxy-4-methyl-1,3,5(10)-estratrien-17β-ol is heated under reflux and nitrogen purging in 20 ml. of toluene with 35 ml. of diisobutylaluminum hydride (20% in toluene) for 30 hours. The reaction mixture is decomposed and worked up according to Example 3. The dried residue is extracted with a methylene chloride-methanol mixture (2:1), concentrated to dryness under vacuum, and crystallized from methanol. Yield: 1.77 g. of 4-methyl-1,3,5(10)-estratriene-1,17β-diol, m.p. 227°–229° C. $[\alpha]_D = +178.2°$ (dioxane); $\epsilon_{281} = 1920$.

EXAMPLE 17

Under agitation and nitrogen purging, 9.36 g. of aluminum chloride is added at 0° C. to a suspension of 8.9 g. of lithium aluminum hydride in 790 ml. of ether; after one hour, the product is filtered off from the thus-formed lithium chloride. The ether filtrate, which contains the aluminum hydride, is added dropwise under nitrogen to a solution of 2.0 g. of 3-methoxy-1,3,5(10),7-estratraen-17β-ol in 50 ml. of toluene. The ether is distilled off, and the reaction mixture is maintained for 17 hours at the reflux temperature of the toluene. Under ice cooling, the mixture is decomposed with 5 ml. of ethyl acetate, then with 5 ml. of ethanol, and furthermore with 5 ml. of ethanol-water mixture (1:1), and the mixture is then worked up analogously to Example 3. The dried residue is extracted with a methylene chloride-methanol mixture, concentrated to dryness under vacuum, and crystallized from methanol, thus obtaining 1.65 g. of 1,3,5(10),7-estratetraene-3,17β -diol, m.p. 172°–175° C. $[\alpha]_D = +202.0°$ (dioxane); $\epsilon_{279} = 2150$.

EXAMPLE 18

0.50 g. of 3-benzyloxy-1,3,5(10),16-estratetraene is stirred in 10 ml. of toluene with 6.5 ml. of di-n-butylaluminum hydride (20% in toluene) for 24 hours at 40° C. under nitrogen purging. The reaction mixture is decomposed and worked up as described in Example 6. The precipitate from the 2% hydrochloric solution is taken up with methylene chloride, the methylene chloride phase is washed neutral, and the solvent is distilled off under vacuum. The remaining oily residue is chromatographed over silica gel and further purified from an ether-hexane mixture. Yield: 0.24 g. of 1,3,5(10),16-estratetraen-3-ol, m.p. 128°–130° C. $[\alpha]_D = +113.8°$ (CHCl$_3$); $\epsilon_{280} = 2060$.

EXAMPLE 19

2.0 g. of rac.-3-methoxy-18-methyl-1,3,5(10),8-estratetraen-17-one is agitated in 20 ml. of toluene with 25 ml. of diethylaluminum hydride (20% in toluene) for 72 hours at 50° C. under nitrogen purging. The reaction mixture is decomposed and worked up as set forth in Example 3. The dried residue is extracted with methanol, concentrated under vacuum, and the remaining oil is crystallized with hexane. Yield: 1.75 g. of rac.-18-methyl-1,3,5(10),8-estratetraene-3,17β-diol; m.p. 179°–181° C.; $\epsilon_{276} = 15,750$.

EXAMPLE 20

2.0 g. of 1-methoxy-17,17-ethylenedioxy-4-methyl-1,3,5(10)-estratriene is heated for 24 hours under reflux and nitrogen purging in 20 ml. of toluene with 25 ml. of diethylaluminum hydride (20% in toluene). The reaction mixture is decomposed and worked up as described in Example 3. The dried residue is extracted with a methylene chloride-methanol mixture (1:1), concentrated to dryness under vacuum, and crystallized from hexane. After recrystallization from methylene chloride-isopropyl ether with carbon, 1.57 g. of 4-methyl-1,3,5(10)-estratriene-1,17β-diol, m.p. 226°–229° C., is obtained. $[\alpha]_D = +177.9°$ (dioxane); $\epsilon_{280} = 1930$.

EXAMPLE 21

2.0 g. of 3-methoxy-1,3,5(10)-estratrien-17α-ol is dissolved in 20 ml. of toluene and heated under reflux and nitrogen purging for 8 hours with 25 ml. of diisobutylaluminum hydride (20% in toluene). The reaction mixture is decomposed and worked up as set forth in Example 6. After purification, 1.15 g. of 3,17α-dihydroxy-1,3,5(10)-estratriene is obtained, m.p. 218°–220° C. $\epsilon_{280} = 2010$; $[\alpha]_D = +54.3°$ (alcohol).

EXAMPLE 22

20 g. of the 3-methoxy steroids set forth below is dissolved in 60 ml. of toluene, or suspended therein, and heated for 6 hours under reflux and nitrogen purging with 300 ml. of diisobutylaluminum hydride (20% in toluene). The reaction mixture is decomposed as described in Example 1. The thus-decomposed residue is combined with 250 ml. of ethanol, washed over kieselguhr with ethanol, and the filtrate is concentrated under vacuum.

a. 3-Methoxy-1,3,5(10),7-estratetraen-17α-ol; yield: 15.4 g.

b. 3-Methoxy-17α-formyloxy-1,3,5(10),7-estratetraene; yield: 13.4 g.

c. 3-Methoxy-17α-acetoxy-1,3,5(10),7-estratetraene; yield: 14.9 g.

The thus-obtained 3,17α-dihydroxy-1,3,5(10),7-estratetraene has a melting point of 201°–203° C. $\epsilon_{278} = 2110$; $[\alpha]_D = +180.3°$ (dioxane).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for cleaving ethers of steroid aromatic alcohols to regenerate the aromatic alcoholic group which comprises reacting the ether in an inert solvent with an aluminum compound of the formula $AlR_1R_2R_3$ wherein $R_1$, $R_2$ and $R_3$ each are hydrogen or alkyl.

2. A process according to claim 1 wherein the aluminum compound is aluminum hydride.

3. A process according to claim 1 wherein $R_1$ and $R_2$ are alike and are alkyl of 1–4 carbon atoms and $R_3$ is H or $R_1$.

4. A process according to claim 3 wherein $R_1$ and $R_2$ are ethyl, n-butyl or isobutyl.

5. A process according to claim 3 wherein $R_1$ and $R_2$ are isobutyl.

6. A process according to claim 1 wherein the aluminum compound is diisobutylaluminum hydride.

7. A process according to claim 1 wherein the steroid is an A-ring aromatic steroid.

8. A process according to claim 7 wherein the ether is an ether of an alcohol of 1–4 carbon atoms.

9. A process according to claim 7 wherein the ether is a methyl ether.

10. A process according to claim 7 wherein $R_1$ and $R_2$ are alike and are alkyl of 1–4 carbon atoms, and $R_3$ is H or $R_1$.

* * * * *